(12) United States Patent
Papas (10) Patent No.: US 11,229,230 B2
(45) Date of Patent: Jan. 25, 2022

(54) ANTIOXIDANT-ENRICHED MULTIVITAMIN COMPOSITION AND METHODS OF USE

(71) Applicant: Callion Pharma, LLC, Jonesborough, TN (US)

(72) Inventor: Konstantinos Andreas Papas, Jonesborough, TN (US)

(73) Assignee: Callion Pharma, LLC, Jonesborough, TN (US)

( * ) Notice: Subject to any disclaimer, the term of this patent is extended or adjusted under 35 U.S.C. 154(b) by 12 days.

(21) Appl. No.: 16/343,062

(22) PCT Filed: Oct. 24, 2017

(86) PCT No.: PCT/US2017/057981
§ 371 (c)(1),
(2) Date: Apr. 18, 2019

(87) PCT Pub. No.: WO2018/081048
PCT Pub. Date: May 3, 2018

(65) Prior Publication Data
US 2019/0281876 A1 Sep. 19, 2019

Related U.S. Application Data

(60) Provisional application No. 62/411,868, filed on Oct. 24, 2016.

(51) Int. Cl.
| | |
|---|---|
| *A23L 33/155* | (2016.01) |
| *A23L 29/00* | (2016.01) |
| *A23L 33/105* | (2016.01) |
| *A61K 9/00* | (2006.01) |
| *A61K 9/20* | (2006.01) |
| *A61K 31/07* | (2006.01) |
| *A61K 31/355* | (2006.01) |
| *A61K 31/375* | (2006.01) |
| *A61K 31/59* | (2006.01) |
| *A61K 31/592* | (2006.01) |
| *A61K 31/122* | (2006.01) |
| *A61K 33/04* | (2006.01) |
| *A61K 31/455* | (2006.01) |
| *A61P 3/02* | (2006.01) |
| *A61K 31/519* | (2006.01) |
| *A61K 31/525* | (2006.01) |
| *A61K 31/714* | (2006.01) |
| *A61K 31/4188* | (2006.01) |

(Continued)

(52) U.S. Cl.
CPC ............ *A23L 33/155* (2016.08); *A23L 29/045* (2016.08); *A23L 29/055* (2016.08); *A23L 33/105* (2016.08); *A61K 9/0053* (2013.01); *A61K 9/20* (2013.01); *A61K 31/01* (2013.01); *A61K 31/047* (2013.01); *A61K 31/065* (2013.01); *A61K 31/07* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/592* (2013.01); *A61K 31/593* (2013.01); *A61K 31/714* (2013.01); *A61K 33/04* (2013.01); *A61K 33/30* (2013.01); *A61P 3/02* (2018.01); *A23V 2002/00* (2013.01); *A23V 2200/314* (2013.01); *A23V 2250/1626* (2013.01); *A23V 2250/1642* (2013.01); *A23V 2250/211* (2013.01); *A23V 2250/213* (2013.01); *A23V 2250/314* (2013.01); *A23V 2250/702* (2013.01); *A23V 2250/705* (2013.01); *A23V 2250/708* (2013.01); *A23V 2250/7046* (2013.01); *A23V 2250/7052* (2013.01); *A23V 2250/7056* (2013.01); *A23V 2250/71* (2013.01); *A23V 2250/712* (2013.01); *A23V 2250/714* (2013.01); *A23V 2250/72* (2013.01)

(58) Field of Classification Search
None
See application file for complete search history.

(56) References Cited

U.S. PATENT DOCUMENTS

| | | | |
|---|---|---|---|
| 2,680,749 A | 6/1954 | Cawley et al. | |
| 5,179,122 A * | 1/1993 | Greene | ................ A61K 31/355 424/489 |

(Continued)

FOREIGN PATENT DOCUMENTS

| | | | |
|---|---|---|---|
| WO | 2006130048 A1 | 12/2006 | |
| WO | 20155063041 A1 | 5/2015 | |

(Continued)

OTHER PUBLICATIONS

NCT01859390 (version 13, published Aug. 26, 2015) (Year: 2015).*
(Continued)

*Primary Examiner* — Craig D Ricci
(74) *Attorney, Agent, or Firm* — Dinsmore & Shohl LLP; Monika Jaensson, Esq.; Jennifer Livingston, Esq.

(57) ABSTRACT

Provided herein are antioxidant-enriched multivitamin compositions comprising vitamin A, vitamin C, vitamin D, vitamin E, vitamin K, thiamin, riboflavin, niacin, vitamin B6, folic acid, vitamin B 12, biotin, pantothenic acid, zinc, selenium, coenzyme Q10, lutein, lycopene, and zeaxanthin for the treatment of fat malabsorption diseases such as cystic fibrosis. Also provided are methods of treating vitamin and micronutrient deficiencies in subjects suffering from cystic fibrosis by administering an antioxidant-enriched multivitamin composition.

2 Claims, 3 Drawing Sheets

(51) Int. Cl.
*A61K 31/065* (2006.01)
*A61K 31/593* (2006.01)
*A61K 31/51* (2006.01)
*A61K 31/4415* (2006.01)
*A61K 31/01* (2006.01)
*A61K 31/047* (2006.01)
*A61K 31/197* (2006.01)
*A61K 33/30* (2006.01)

(56) References Cited

U.S. PATENT DOCUMENTS

| | | | |
|---|---|---|---|
| 6,358,544 | B1 | 3/2002 | Henry, Jr. et al. |
| 9,439,913 | B1 | 9/2016 | Walters |
| 2004/0197430 | A1* | 10/2004 | Meyrowitz .......... A61K 36/889 |
| | | | 424/756 |
| 2005/0074445 | A1 | 4/2005 | Papas et al. |
| 2005/0214383 | A1* | 9/2005 | Bubnis ................ A61K 31/375 |
| | | | 424/641 |
| 2007/0141203 | A1 | 6/2007 | Cook |
| 2010/0227001 | A1 | 9/2010 | Demeter |
| 2012/0269868 | A1* | 10/2012 | Faerstein .............. A23L 33/115 |
| | | | 424/400 |

FOREIGN PATENT DOCUMENTS

| | | |
|---|---|---|
| WO | 2016053955 A1 | 4/2016 |
| WO | 2016149655 A1 | 9/2016 |

OTHER PUBLICATIONS

Sagel et al (J Cystic Fibrosis 10:31-36, 2011) (Year: 2011).*
International Search Report pertaining to Application No. PCT/US17/57981 dated Jan. 2, 2018.
Extended European Search Report (EESR) for corresponding EP Application No. 17866272.2 prepared May 25, 2020.
Scott D. Sagel et al., Effect of an antioxidant-rich multivitamin supplement in cystic fibrosis; Journal of Cystic Fibrosis, 2011, vol. 10, No. 1, pp. 31-36.
Douglas Homnick et al., Carotenoid levels in normal children and in children with cystic fibrosis; Journal of Pediatrics, 1993, vol. 122, No. 5, pp. 703-707.

* cited by examiner

|  | Antioxidant (N=36) | Control (N=37) |
|---|---|---|
| Gender, n (%) | | |
|    Female | 20 (55.6%) | 20 (54.1%) |
| Age (years), mean (SD) | 22.3 (8.9) | 22.9 (9.5) |
| Age distribution, n (%) | | |
|    >= 10 -18 yrs | 13 (36.1%) | 16 (43.2%) |
|    >= 18 -30 yrs | 17 (47.2%) | 11 (29.7%) |
|    >30 yrs | 6 (16.7%) | 10 (27.0%) |
| Race, n (%) | | |
|    Caucasian | 34 (94.4%) | 30 (81.1%) |
|    Hispanic | 1 (2.8%) | 5 (13.5%) |
|    African-American | 1 (2.8%) | 1 (2.7%) |
|    Unknown/Other | 0 (0%) | 1 (2.7%) |
| Genotype, n (%) | | |
|    F508del Homozygous | 23 (63.9%) | 16 (43.2%) |
|    F508del Heterozygous | 9 (25.0%) | 18 (48.6%) |
|    Other/Unknown [1] | 4 (11.1%) | 3 (8.1%) |
| BMI ($kg/m^2$), mean (SD) | 21.9 (4.4) | 21.0 (3.2) |
| $FEV_1$ %Predicted [2], mean (SD) | 74.9% (15.4) | 76.3% (13.4) |
| $FEV_1$ %Predicted distribution, n (%) | | |
|    <=70% | 11 (30.6%) | 10 (27.0%) |
|    70-<=90% | 18 (50.0%) | 22 (59.5%) |
|    >90% | 7 (19.4) | 5 (13.5%) |
| History of Meconium Ileus, n(%) | | |
|    Yes | 4 (11.1%) | 4 (10.8%) |
| Chronic Inhaled Antibiotics [3], n(%) | | |
|    Yes | 20 (55.6%) | 20 (54.1%) |
| Chronic Azithromycin [3], n(%) | | |
|    Yes | 16 (44.4%) | 18 (48.6%) |

[1] Other refers to subjects with either two known, non-F508del CF mutations, or one known, non F508del CF mutation and one unidentified allele which has not been classified as a CF mutation.
[2] $FEV_1$ % predicted is calculated using the Wang (Female < 16 years, Male < 18 years) or Hankinson equations (Female ≥ 16 years, Male ≥ 18 years).
[3] Chronic is defined as initiated ≥ 8 weeks prior to randomization.

ANTIOXIDANT-ENRICHED MULTIVITAMIN COMPOSITION AND METHODS OF USE

CROSS-REFERENCE TO RELATED APPLICATION

The present application claims priority to U.S. Provisional Application 62/411,868 filed Oct. 24, 2016, the entire disclosure of which is incorporated herein by this reference.

TECHNICAL FIELD

The presently disclosed subject matter relates to antioxidant-enriched multivitamin compositions suitable as dietary supplements for the treatment of subjects suffering from conditions associated with malabsorption of fat-soluble vitamins, including cystic fibrosis.

BACKGROUND

Certain diseases, conditions, surgeries, procedures, and medications are associated with malabsorption of fat, which can lead to serious deficiencies of the fat-soluble vitamins and micronutrients. For example, individuals suffering from cholestatic liver disease, cystic fibrosis, Crohn's Disease, post-bariatric procedures, chronic pancreatitis, pancreatic diseases or resection, inflammatory bowel disease, HIV, short bowel syndrome, and other conditions may experience severe deficiencies of fat-soluble vitamins and micronutrients.

Deficiency of fat-soluble vitamins and nutrients has well documented adverse health effects that lead to increased morbidity and mortality. Vitamin E deficiency in cholestatic liver disease can cause a progressive neurologic syndrome including cerebellar ataxia, posterior column dysfunction, and peripheral neuropathy. Vitamin A deficiency can lead to visual impairment from impaired dark adaptation of the eyes and night blindness, to xerophthalmia, keratomalacia, and blindness. Vitamin A also plays a critical role in growth, immune function, and gene expression. Growth retardation and a decreased immune function and increased infections are common among children with vitamin A deficiency. Vitamin D deficiency is well known to cause metabolic bone diseases, including osteoporosis. Vitamin K deficiency is well known to cause bleeding, including intracranial hemorrhage, and can be a catastrophic in infants, but is also required for the gamma-carboxylation of osteocalcin and bone health.

In addition to the well described deficiency states of the fat-soluble vitamins A, D, E and K, malabsorption and deficiency of other fat-soluble micronutrients is also common in the above-described diseases and conditions, including but not limited to carotenoids, coenzyme Q10, omega-3 fatty acids, and certain polyphenols. Deficiency of these fat-soluble micronutrients has been documented in conditions of malabsorption, including cystic fibrosis. These micronutrients likely play an important role in normal health and immune function through both antioxidant and non-antioxidant mechanisms.

The deficiency of fat-soluble vitamins and micronutrients in these disease states often leads to a diminished antioxidant status. Further, the underlying disease condition is often associated with increased oxidative stress, inflammation and/or infection leading to a further increased requirement of these fat-soluble vitamins and micronutrients. In combination, poor antioxidant status and increased oxidative stress/inflammation can lead to poor health outcomes.

Airway inflammation plays a central role in the progression of cystic fibrosis lung disease, which is characterized by chronic bacterial infection, chronic inflammation, and progressive destruction of the lung architecture leading to a decrease in life expectancy. Elevated reactive oxygen species is well documented in cystic fibrosis by elevated concentrations of plasma malondialdehyde, exhaled breath pentane and ethane, and plasma hydroperoxides and by depletion of the major lipoperoxidation substrates, such as linoleic and arachidonic acids. These reactive oxygen species released by neutrophils and/or bacterial pathogens in the lungs overwhelm the depleted systemic antioxidants, leading to a further inflammation and damage.

There are two main hurdles to finding an effective fat-soluble vitamin/micronutrient treatment to reduce stress in conditions such as cystic fibrosis (CF). First, absorption of these fat-soluble compounds is limited by the underlying disease. Evidence shows that supplementation of high amounts of vitamins does not often normalize plasma and or tissue levels when absorption mechanisms are impaired. Feranchak et al. (1999) demonstrated that biochemical deficiency of one or more fat-soluble vitamins was present in 45.8% of patients at diagnosis of CF between ages 4 and 8 weeks. Despite supplementation with regular multivitamins, persistent deficiency of vitamin A (11.1%), vitamin D (12.5%), or vitamin E (57.1%) was common over a 10 year follow-up period. Children with severe cholestasis are unable to absorb these massive doses of available preparations of vitamin E, leading to neurological issues. Achieving normal blood and tissue levels of these fat-soluble compounds is critical to an effective treatment.

Second, supplying the appropriate combination of fat-soluble vitamins and micronutrients to function complementarily and synergistically together and reach the affected target tissue is critical in the successful improvement of a clinically relevant outcome in the disease condition. There are a myriad of fat-soluble compounds available in the normal human diet and it would be impossible to supplement patients with all of these compounds. It is a significant challenge to (1) select the appropriate compounds based on the disease state, (2) develop formulations that function as orally effective supplements, (3) formulate compositions comprising agents that don't interact with each other, and (4) formulate compositions that don't affect normal reactive oxygen species physiological responses as part of signaling processes and defense mechanisms, in order to improve clinically relevant health outcomes. Only three of 87 trials in a Cochrane Review which examined the effect of supplementation in cystic fibrosis met their established selection criteria for analysis and none reported an improvement in lung function or a decreased time to exacerbation despite increases in the supplemented vitamin or micronutrient levels. The use of inhaled glutathione in cystic fibrosis, a key antioxidant that is decreased in the lung tissue of cystic fibrosis patients, has not been effective in studies and the Cystic Fibrosis Foundation has discontinued the treatment from its pipeline. Oral treatment with the precursor molecule, N-acetylcysteine, did not improve lung function in a Phase II clinical study (although lung function was maintained).

The need exists to develop an antioxidant-enriched multivitamin composition for the treatment of subjects suffering from conditions associated with malabsorption of fat, including cystic fibrosis.

SUMMARY

Accordingly, provided herein is an antioxidant-enriched multivitamin composition comprising an absorbable and effective formulation of fat-soluble vitamins and micronutrients, and methods of use. The presently disclosed compositions provide an effective treatment for conditions of malabsorption, normalize the levels of these constituents, and improve the underlying oxidative/stress inflammatory disease state, as evidenced by a statistically significant improvement in a clinically relevant outcome to the disease state. The disclosed compositions are directed to oral dietary supplements and methods of use in the treatment of diseases associated with fat malabsorption, particularly cystic fibrosis.

In one embodiment, an oral dosage form of a multivitamin for subjects suffering from cystic fibrosis is provided, comprising an effective amount of each of: vitamin A, vitamin C, vitamin D, vitamin E, vitamin K, thiamin, riboflavin, niacin, vitamin B6, folic acid, vitamin B12, biotin, pantothenic acid, zinc, selenium, coenzyme Q10, lutein, lycopene, and zeaxanthin.

In another embodiment, a method is provided for supplementing nutrients in a subject in need thereof suffering from cystic fibrosis, comprising administering to the subject an oral dosage form of a multivitamin for subjects suffering from cystic fibrosis comprising an effective amount of each of: vitamin A, vitamin C, vitamin D, vitamin E, vitamin K, thiamin, riboflavin, niacin, vitamin B6, folic acid, vitamin B12, biotin, pantothenic acid, zinc, selenium, coenzyme Q10, lutein, lycopene, and zeaxanthin.

These and other objects, features, embodiments, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by those of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±25%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The terms "treat," "treatment," and "treating," as used herein, refer to a method of alleviating or abrogating a disease, disorder, deficiency, and/or symptoms thereof.

Provided herein are absorbable and effective multivitamin compositions comprising fat-soluble vitamins and micronutrients. The presently disclosed compositions provide an effective treatment for conditions of malabsorption and normalize the levels of these constituents. The compositions also improve the underlying oxidative stress inflammatory disease state, as evidenced by a statistically significant improvement in a clinically relevant outcome, namely, time to first pulmonary exacerbation.

The presently disclosed compositions comprise the fat-soluble vitamins A, D, E and K, other specifically chosen fat-soluble micronutrients, as well as water-soluble vitamins and minerals. Water-soluble vitamins and minerals are included in the formulation to provide a comprehensive multivitamin and mineral supplement, as is commonly used in this population. The addition of water-soluble vitamins and minerals in the formulation precludes the need for an additional vitamin supplement to provide commonly used multivitamin components and increases commercial viability of the product.

Compositions

The vitamin and micronutrient components of an absorbable and effective multivitamin composition for the treatment of diseases associated with fat malabsorption, including cystic fibrosis, are described below. The oral dosage form comprises an effective amount of each of: vitamin A, vitamin C, vitamin D, vitamin E, vitamin K, thiamin, riboflavin, niacin, vitamin B6, folic acid, vitamin B12, biotin, pantothenic acid, zinc, selenium, coenzyme Q10, lutein, lycopene, and zeaxanthin.

Vitamin A refers to a group of fat-soluble retinoids, including retinol, retinyl esters (such as retinyl palmitate), retinal, and retinoic acid. Vitamin A is implicated in growth and development, immune system function, gene expression, reproduction, and vision. Vitamin A functions in the retina, whereby light is transduced into the neural signals necessary for vision. Retinoic acid is required to maintain normal differentiation of the cornea and conjunctival membranes. Retinoic acid is also required to regulate the expression of various genes that encode for structural proteins (e.g., skin keratins), enzymes (e.g., alcohol dehydrogenase), extracellular matrix proteins (e.g., laminin), and retinol binding proteins and receptors. Vitamin A deficiency is associated with impaired vision, including night blindness and xerophthalmia, and is important for pregnant and breast-feeding women. Two forms of vitamin A are available in the human diet: preformed vitamin A (retinol and retinyl esters) and provitamin A carotenoids (beta-carotene, alpha carotene, gamma-carotene, and beta cryptoxanthin). The body converts these provitamin carotenoids into vitamin A. In certain embodiments of the present compositions, vitamin A is provided in a form selected from the group consisting of retinyl esters (such as retinyl palmitate), beta-carotene, and combinations thereof. A unit dosage disclosed herein may comprise from about 4,000 to about 20,000 IU vitamin A; from about 6,000 to about 20,000 IU; from about 8,000 to about 20,000 IU; from about 10,000 to about 20,000 IU; from about 12,000 to about 20,000 IU; from about 14,000 to about 20,000 IU; from about 16,000 to about 20,000 IU; or from about 17,000 to about 19,000 IU vitamin A. In a specific embodiment, the unit dosage comprises about 18,000 IU vitamin A. In a very specific embodiment, the unit dosage comprises 18,167 IU vitamin A. In another very specific embodiment, the unit dosage comprises about 1500 IU retinyl palmitate and about 16,667 IU beta-carotene. In an embodiment, the total IU vitamin A comprises from about 5% to about 25% retinyl palmitate and from about 75% to about 95% beta-carotene. In a specific embodiment, the total IU vitamin A comprises about 8% retinyl palmitate and about 92% beta-carotene.

Vitamin D is a fat-soluble vitamin that enhances intestinal absorption of calcium and phosphorus. Vitamin D has other roles in the body, including modulation of cell growth, pro-differentiation, neuromuscular and immune function, and reduction of inflammation. Vitamin D comprises various forms, including the two primary forms in humans, cholecalciferol (vitamin $D_3$) and ergocalciferol (vitamin $D_2$). Vitamin $D_3$ is produced photochemically in the skin upon exposure to sunlight. Vitamin D is also ingested from diet or supplements. Deficiency of vitamin D results in impaired bone mineralization and bone softening diseases, including rickets and osteomalacia. In one embodiment, the compositions disclosed herein comprise vitamin D in a form selected from the group consisting of cholecalciferol, ergocalciferol, and combinations thereof. In a specific embodiment, vitamin D is in the form of cholecalciferol. A unit dosage disclosed herein may comprise from about 1,000 to about 6,000 IU vitamin D; from about 2,000 to about 5,000 IU; or from about 2,000 to about 4,000 IU vitamin D. In a specific embodiment, the unit dosage comprises about 3,000 IU vitamin D. In another specific embodiment, the unit dosage comprises about 1,600 IU vitamin D.

Vitamin E refers to a group of eight fat-soluble compounds that include four tocopherols and four tocotrienols. Each is identified by a prefix alpha ($\alpha$), beta ($\beta$), gamma ($\gamma$), and delta ($\delta$). Alpha-tocopherol is an antioxidant that protects cell membranes. Vitamin E is also implicated in gene expression and neurological functions. Vitamin E is ingested from diet or supplements. Deficiency of vitamin E can result in ataxia, retinopathy, impaired immune response, peripheral neuropathy, and red blood cell destruction, among other conditions.

Tocopherol forms of vitamin E particularly useful in supplementation include $\alpha$-tocopherol and d-$\alpha$-tocopherol polyethylene glycol 1000 succinate (TPGS). TPGS is a water-soluble derivative of the natural form of vitamin E, d-$\alpha$-tocopherol, produced by the esterification of crystalline d-$\alpha$-tocopheryl succinate by polyethylene glycol 1000. TPGS is known to enhance the absorption of coadministered fat-soluble compounds and small molecules.

TPGS is particularly useful in enhancing delivery of lipophilic compounds. In particular, TPGS has been shown to increase vitamin D absorption in individuals suffering from chronic childhood cholestasis. Argao et al., *d-Alpha-tocopherol polyethylene glycol*-1000 *succinate enhances the absorption of vitamin D in chronic cholestatic liver disease of infancy and childhood*, Ped. Res. 31(2):146-50 (1992). As such, vitamin E in the form of TPGS has particular utility in the formulation of vitamin supplements for individuals suffering from severe malabsorption of fat-soluble vitamins. Further, the enhanced delivery of lipophilic compounds by TPGS is particularly useful in correcting vitamin deficiencies where increasing amounts of fat-soluble vitamins are ineffective and may lead to toxicity. TPGS advantageously enhances delivery of lipophilic compounds, thereby minimizing the risk of toxicity across the spectrum of malabsorption. The compositions disclosed herein comprise vitamin E in the form of alpha-tocopherol or mixed tocopherols, either alone or in combination with TPGS. Mixed tocopherols comprise one or more of alpha-, beta-, gamma-, and delta-tocopherol. In one embodiment, a unit dosage disclosed herein comprises from about 50 to about 400 IU total vitamin E in a form selected from the group consisting of alpha-tocopherol, mixed tocopherols, TPGS, and combinations thereof. In another embodiment, the composition comprises from about 75 to about 300 IU; from about 100 to about 300 IU; or from about 100 to about 200 IU total vitamin E. More specifically, the composition comprises about 150 IU total vitamin E. In one embodiment, the total vitamin E comprises from about 0 to about 200 mg mixed tocopherols and from about 0 to 500 mg TPGS. In a specific embodiment, the total vitamin E comprises about 80 mg mixed tocopherols and about 200 mg TPGS.

Vitamin K refers to a group of fat-soluble vitamins that facilitate blood coagulation and binding of calcium in bone and other tissues. Vitamin K also plays an essential role in the conversion of certain residues in proteins into biologically active forms. Vitamin K includes two natural forms, $K_1$ and $K_2$. Vitamin $K_1$ is also known as phylloquinone, phytomenadione, or phytonadione and is found in abundance in green, leafy vegetables. Vitamin $K_2$ is the main storage form of vitamin K in animals and comprises several subtypes, or menaquinones, characterized by the number of isoprenoid residues in their side chains. Menaquinones are abbreviated MK-n, wherein M indicates menaquinone, K indicates vitamin K, and n represents the number of isoprenoid side chain residues. Vitamin K is also available in synthetic forms, including $K_3$, $K_4$, and $K_5$, although vitamin $K_3$ has shown toxicity. Vitamin K is ingested from diet or supplements and vitamin $K_2$ can be produced in the gut. Deficiency of vitamin K, generally the result of a condition resulting in malabsorption of the vitamin, can result in coagulopathy, osteoporosis, and coronary heart disease. Populations at risk for vitamin K deficiency include those suffering from liver disease, cystic fibrosis, inflammatory bowel disease, or who have had abdominal surgeries. Secondary vitamin K deficiency can occur in those suffering from bulemia, those on strict diets, or individuals taking anticoagulants or certain other drugs. In one embodiment, a unit dosage provided herein comprises from about 0.25 to about 5 mg vitamin K. In another embodiment, a unit dosage comprises from about 0.5 to about 5 mg; from about 0.5 to about 3 mg; from about 0.5 to about 2 mg; or from about 0.5 to about 1.5 mg vitamin K. In a more specific embodiment, the unit dosage comprises about 1 mg vitamin K. In one embodiment, vitamin K is in a form selected from the group consisting of phytonadione, menaquinone, and combinations thereof. In a specific embodiment, vitamin K is in the form of phytonadione.

Selenium is a trace mineral that functions through selenoproteins, several of which defend against oxidative stress. As such, selenium plays a role as a dietary antioxidant. Although the function of all selenoproteins has not yet been characterized, selenium has been found to regulate both thyroid hormone actions and the redox status of vitamin C and other molecules. In certain embodiments, a unit dosage of a supplement disclosed herein comprises from about 25 to about 200 mcg selenium. In another embodiment, a unit dosage comprises from about 50 to about 175 mcg; from about 50 to about 150 mcg; from about 50 to about 125 mcg; or from about 50 to about 100 mcg selenium. In a more specific embodiment, the unit dosage comprises about 75 mcg selenium.

Coenzyme Q10 (CoQ10) is a fat-soluble micronutrient that primarily functions as an antioxidant, a membrane stabilizer, and as a cofactor in many metabolic pathways, particularly in the production of adenosine triphosphate (ATP) in oxidative respiration. CoQ10 increases plasma levels of high density lipoprotein (HDL) cholesterol, vitamin E, and vitamin C; and decreases levels of total cholesterol, low density lipoprotein (LDL) cholesterol, and products of lipid peroxidation such as thiobarbituric acid reactive substances (TBARS), malondialdehyde, and diene conjugates. Additionally, CoQ10 acts as a potent antioxidant in mitochondria and lipid membranes by scavenging free oxygen radicals, thereby protecting membrane phospholipids, serum polyunsaturated fatty acids and lipoproteins as LDL from free radical induced oxidative damage. Further, CoQ10 recycles oxidized α-tocopheryl back to α-tocopherol, and acts as an electron carrier in the mitochondrial adenosine triphosphate synthesis of all cells in the body. Embodiments of unit dosages described herein comprise from about 5 to about 100 mg coenzyme Q10. In other embodiments, a unit dosage comprises from about 5 to about 80 mg; from about 5 to about 70 mg; from about 5 to about 50 mg; from about 5 to about 35 mg; or from about 5 to about 30 mg coenzyme Q10. In a specific embodiment, a unit dosage comprises about 25 mg coenzyme Q10. In another specific embodiment, the unit dosage comprises about 10 mg coenzyme Q10.

Carotenoids are natural pigments found in plants that are usually fat-soluble due presence of long unsaturated aliphatic chains. Provitamin A carotenoids, such as beta-carotene, alpha-carotene and beta-cryptoxanthin can be converted to retinol in the body, as described above. Other carotenoids are not metabolized into vitamin A in the body. These include xanthophylls, such as lutein and zeaxanthin, which play a role in the macular pigment; and lycopene, a bright red carotene found in tomatoes and other red fruits and vegetables. Some carotenoids function as precursors or as vitamin A, some have antioxidant functions, and some function as both. In one embodiment, a unit dosage as provided herein comprises from about 1 to about 10 mg lutein. In another embodiment, the unit dosage comprises from about 2 to about 10 mg; from about 3 to about 10 mg; from about 3 to about 8 mg; from about 3 to about 6 mg; or from about 4 to about 6 mg lutein. In a specific embodiment, the unit dosage comprises about 5 mg lutein.

In one embodiment, a unit dosage as provided herein comprises from about 0.25 to about 5 mg lycopene. In other embodiments, the unit dosage comprises from about 0.5 to about 5 mg; from about 0.5 to about 4 mg; from about 0.5 to about 3 mg; from about 0.5 to about 2 mg; from about 0.5 to about 1.5 mg lycopene. In a specific embodiment, the unit dosage comprises about 1 mg lycopene.

In one embodiment, a unit dosage as provided herein comprises from about 0.25 to about 5 mg zeaxanthin. In other embodiments, the unit dosage comprises from about 0.25 to about 4 mg; from about 0.25 to about 3 mg; from about 0.25 to about 2 mg; from about 0.5 to about 2 mg; from about 0.5 to about 1.5 mg; from about 0.5 to about 1.25 mg; or from about 0.5 to about 1 mg zeaxanthin. In a specific embodiment, the unit dosage comprises about 0.75 mg zeaxanthin.

Other vitamins and micronutrients suitable for inclusion in the present compositions include B vitamins, such as thiamin, riboflavin, niacin, B6, folic acid, B12, biotin, and pantothenic acid; vitamin C; and zinc.

In one embodiment, a unit dosage comprises from about 0.5 to about 5 mg thiamin. In other embodiments, the unit dosage comprises from about 0.5 to about 4 mg; from about 0.5 to about 3 mg; from about 0.5 to about 2 mg; from about 0.5 to about 1 mg; from about 1 to about 2 mg; or from about 1.25 to about 1.75 mg thiamin. In a specific embodiment, the unit dosage comprises about 1.5 mg thiamin. In another specific embodiment, the unit dosage comprises about 0.75 mg thiamin.

In one embodiment, a unit dosage comprises from about 0.5 to about 5 mg riboflavin. In other embodiments, the unit dosage comprises from about 0.5 to about 4 mg; from about 0.5 to about 3 mg; from about 0.5 to about 2 mg; from 1 to about 2 mg; or from about 1.5 to about 2 mg riboflavin. In a specific embodiment, the unit dosage comprises about 1.7 mg riboflavin.

In one embodiment, a unit dosage comprises from about 5 to about 40 mg niacin. In other embodiments, the unit dosage comprises from about 5 to about 30 mg; from about 5 to about 20 mg; from about 5 to about 15 mg; from about 7 to about 12 mg; or from about 8 to about 12 mg. In a specific embodiment, the unit dosage comprises about 10 mg niacin.

In one embodiment, a unit dosage comprises from about 0.5 to about 4 mg vitamin B6. In other embodiments, the unit dosage comprises from about 1 to about 3 mg; from about 1 to about 2.5 mg; from about 1 to about 2 mg; or from about 1.5 to about 2 mg vitamin B6. In a specific embodiment, the unit dosage comprises about 1.9 mg vitamin B6.

In one embodiment, a unit dosage comprises from about 100 to about 1000 mcg folic acid. In other embodiments, the unit dosage comprises from about 100 to about 800 mcg; from about 100 to about 600 mcg; from about 100 to about 400 mcg; from about 100 to about 300 mcg; or from about 150 to about 250 mcg folic acid. In a specific embodiment, the unit dosage comprises about 200 mcg folic acid.

In one embodiment, a unit dosage comprises from about 2 to about 50 mcg vitamin B12. In other embodiments, the unit dosage comprises from about 5 to about 40 mcg; from about 5 to about 30 mcg; from about 5 to about 20 mcg; from about 5 to about 15 mcg; from about 10 to about 15 mcg; or from about 11 to about 13 mcg vitamin B12. In a specific embodiment, the unit dosage comprises about 12 mcg vitamin B12.

In one embodiment, a unit dosage comprises from from about 50 to about 1200 mcg biotin. In other embodiments, the unit dosage comprises from about 50 to about 1000 mcg; from about 50 to about 800 mcg; from about 50 to about 600 mcg; from about 50 to about 400 mcg; from about 50 to about 200 mcg; from about 50 to about 150 mcg; or from about 75 to about 125 mcg biotin. In a specific embodiment, the unit dosage comprises about 100 mcg biotin.

In one embodiment, a unit dosage comprises from about 3 to about 20 mg pantothenic acid. In other embodiments, the unit dosage comprises from about 3 to about 15 mg; from about 5 to about 15 mg; from about 10 to about 15 mg; or from about 11 to about 13 mg pantothenic acid. In a specific embodiment, the unit dosage comprises about 12 mg pantothenic acid.

In one embodiment, a unit dosage comprises from about 50 to about 150 mg vitamin C. In other embodiments, the unit dosage comprises from about 50 to about 125 mg; from about 50 to about 100 mg; from about 50 to about 125 mg; from about 50 to about 100 mg; or from about 60 to about 80 mg vitamin C. In a specific embodiment, the unit dosage comprises about 75 mg vitamin C.

In one embodiment, a unit dosage comprises from about 3 to about 30 mg zinc. In other embodiments, the unit dosage comprises from about 5 to about 20 mg; from about 5 to about 15 mg; from about 7 to about 12 mg; or from about 9 to about 11 mg zinc. In a specific embodiment, the unit dosage comprises about 10 mg zinc. In another specific embodiment, the unit dosage comprises about 9 mg zinc.

In one embodiment, an oral dosage form of a multivitamin for treating a subject suffering from cystic fibrosis is provided, comprising an effective amount of each of: vitamin A, vitamin D, vitamin E, vitamin K, selenium, and coenzyme Q10. In a specific embodiment, the oral dosage form comprises: from about 4,000 to about 20,000 IU vitamin A; from about 1,000 to about 6,000 IU vitamin D; from about 50 to about 400 IU vitamin E in a form selected from the group consisting of mixed tocopherols, vitamin E TPGS, and combinations thereof; from about 0.25 to about 5 mg vitamin K; from about 25 to about 200 mcg selenium; and from about 5 to about 40 mg coenzyme Q10. In a more specific embodiment, the oral dosage form comprises: about 18,167 IU vitamin A; about 3,000 IU vitamin D; about 150 IU vitamin E comprising about 80 mg mixed tocopherols and about 200 mg TPGS; about 1 mg vitamin K; about 75 mcg selenium; and about 10 mg coenzyme Q10. Optionally, the vitamin A comprises the provitamin A carotenoid, beta-carotene.

In another embodiment, an oral dosage form of a multivitamin for treating a subject suffering from cystic fibrosis is provided, comprising an effective amount of each of: vitamin A, vitamin C, vitamin D, vitamin E, vitamin K, thiamin, riboflavin, niacin, vitamin B6, folic acid, vitamin B12, biotin, pantothenic acid, zinc, selenium, coenzyme Q10, lutein, lycopene, and zeaxanthin. Optionally, the vitamin A comprises the provitamin A carotenoid, beta-carotene. Optionally, the vitamin E comprises mixed tocopherols and TPGS.

In certain embodiments, the composition is substantially free of other vitamins and micronutrients.

In certain embodiments, any of the unit dosages described herein are provided in the form of a liquid, a softgel, a tablet, a chewable tablet, a bar, a strip, a sublingual dosage form, or a gummy dosage form. In a specific embodiment, the unit dosage is a softgel or a tablet.

The term "carrier," as used herein, includes pharmaceutically acceptable carriers, excipients, or stabilizers which are nontoxic to the subject being exposed thereto at the dosages and concentrations employed. In one embodiment, the compositions described herein comprise at least one pharmaceutically acceptable carrier selected from the group consisting of polymers, resins, plasticizers, fillers, lubricants, diluents, solvents, co-solvents, buffer systems, surfactants, preservatives, sweetening agents, flavoring agents, pharmaceutical grade dyes or pigments, viscosity agents and combinations thereof. Suitable pharmaceutical carriers are well-known in the art. See, for example, *Handbook of Pharmaceutical Excipients, Sixth Edition*, edited by Raymond C. Rowe (2009). Further, the skilled artisan will appreciate that certain carriers may be more desirable or suitable for certain modes of administration of an active ingredient. It is within the purview of the skilled artisan to select the appropriate carriers for a given composition.

Also provided herein are methods for supplementing nutrients in a subject suffering from a disease or condition associated with fat malabsorption, such as cystic fibrosis, said methods comprising administering to the subject any of the oral dosage compositions described herein. The frequency of administration may range from once weekly, twice weekly, three times weekly, four times weekly, 5 times weekly, 6 times weekly, daily, or twice daily. At each administration, the subject may receive one or two oral dosage forms, as recommended by the skilled artisan. The skilled artisan will appreciate that frequency of administration and number of oral dosage forms administered can be selected according to the particular subject's needs.

A method of treating cystic fibrosis in a subject in need thereof is also provided, comprising administering to the subject an oral dosage form of the multivitamin compositions described herein. The frequency of administration may range from once weekly, twice weekly, three times weekly, four times weekly, 5 times weekly, 6 times weekly, daily, or twice daily. At each administration, the subject may receive one or two oral dosage forms, as recommended by the skilled artisan. The skilled artisan will appreciate that frequency of administration can be selected according to the particular subject's needs.

Administering a composition of the present disclosure to a subject suffering from cystic fibrosis significantly and advantageously increases the time to first pulmonary exacerbation in the subject.

EXAMPLES

The following examples are given by way of illustration and are in no way intended to limit the scope of the present invention.

Example 1

Antioxidant-Enriched Multivitamin Compositions
Formulation 1:

| | |
|---|---|
| Vitamin A | 4,000 to 20,000 IU, including from about 5% to about 25% retinyl palmitate and from about 75% to about 95% beta-carotene |
| Vitamin D | 1,000 to 6,000 IU |
| Vitamin E | 50 to 400 IU, including from about 0 to about 200 mg mixed tocopherols and from about 0 to about 500 mg TPGS |
| Vitamin K | 0.25 to 5 mg |
| Selenium | 25 to 200 mcg |
| Coenzyme Q10 | 5 to 100 mg |

Formulation 2:

| Vitamin A | 18,167 IU, including about 8% retinyl palmitate and about 92% beta-carotene |
| --- | --- |
| Vitamin D | 3,000 IU |
| Vitamin E | 150 IU, including 80 mg mixed tocopherols 200 mg TPGS |
| Vitamin K | 1 mg |
| Selenium | 75 mcg |
| Coenzyme Q10 | 10 mg |

Formulation 3:

| Vitamin A | 4,000 to 20,000 IU, including from about 5% to about 25% retinyl palmitate and from about 75% to about 95% beta-carotene |
| --- | --- |
| Vitamin C | 50 to 150 mg |
| Vitamin D | 1,000 to 6,000 IU |
| Vitamin E | 50 to 400 IU, including from about 0 to about 200 mg mixed tocopherols and from about 0 to about 500 mg TPGS |
| Vitamin K | 0.25 to 5 mg |
| Thiamin | 0.5 to 5 mg |
| Riboflavin | 0.5 to 5 mg |
| Niacin | 5 to 40 mg |
| Vitamin B6 | 0.5 to 4 mg |
| Folic Acid | 100 to 1,000 mcg |
| Vitamin B12 | 2 to 50 mcg |
| Biotin | 50 to 1200 mcg |
| Pantothenic acid | 3 to 20 mg |
| Zinc | 3 to 30 mg |
| Selenium | 25 to 200 mcg |
| Coenzyme Q10 | 5 to 100 mg |
| Lutein | 1 to 10 mg |
| Lycopene | 0.25 to 5 mg |
| Zeaxanthin | 0.25 to 5 mg |

Formulation 4 (Softgel):

| Vitamin A | 18167 IU, including 8% retinyl palmitate and 92% beta-carotene |
| --- | --- |
| Vitamin C | 75 mg |
| Vitamin D | 1,600 IU |
| Vitamin E | 150 IU, including 80 mg mixed tocopherols and 200 mg TPGS |
| Vitamin K | 1 mg |
| Thiamin | 0.75 mg |
| Riboflavin | 1.7 mg |
| Niacin | 10 mg |
| Vitamin B6 | 1.9 mg |
| Folic Acid | 200 mcg |
| Vitamin B12 | 12 mcg |
| Biotin | 100 mcg |
| Pantothenic acid | 12 mg |
| Zinc | 9 mg |
| Selenium | 75 mcg |
| Coenzyme Q10 | 25 mg |
| Lutein | 5 mg |
| Lycopene | 1 mg |
| Zeaxanthin | 0.75 mg |

Formula 5 (Softgel):

| Vitamin A | 18167 IU, including 8% retinyl palmitate and 92% beta-carotene |
| --- | --- |
| Vitamin C | 75 mg |
| Vitamin D | 3,000 IU |
| Vitamin E | 150 IU, including 80 mg mixed tocopherols and 200 mg TPGS |
| Vitamin K | 1 mg |
| Thiamin | 1.5 mg |
| Riboflavin | 1.7 mg |
| Niacin | 10 mg |
| Vitamin B6 | 1.9 mg |
| Folic Acid | 200 mcg |
| Vitamin B12 | 12 mcg |
| Biotin | 100 mcg |
| Pantothenic acid | 12 mg |
| Zinc | 10 mg |
| Selenium | 75 mcg |
| Coenzyme Q10 | 10 mg |
| Lutein | 5 mg |
| Lycopene | 1 mg |
| Zeaxanthin | 0.75 mg |

Example 2

Clinical Trial

In a multicenter, randomized, double-blind, controlled trial, pancreatic insufficient cystic fibrosis (CF) subjects were randomized to 16 weeks of an antioxidant-enriched multivitamin (Formula 4 above) or a control multivitamin. The control formula used in the study was as follows:

Control Formulation:

| Vitamin A | 2,500 IU as retinyl palmitate |
| --- | --- |
| Vitamin C | — |
| Vitamin D | 800 IU |
| Vitamin E | 200 IU as d-alpha-tocopherol |
| Vitamin K | 200 mcg |
| Thiamin | 0.75 mg |
| Riboflavin | 1.7 mg |
| Niacin | 10 mg |
| Vitamin B6 | 1.9 mg |
| Folic Acid | 200 mcg |
| Vitamin B12 | 12 mcg |
| Biotin | — |
| Pantothenic acid | 12 mg |
| Zinc | — |
| Selenium | — |
| Coenzyme Q10 | — |
| Lutein | — |
| Lycopene | — |
| Zeaxanthin | — |

Figure 1:
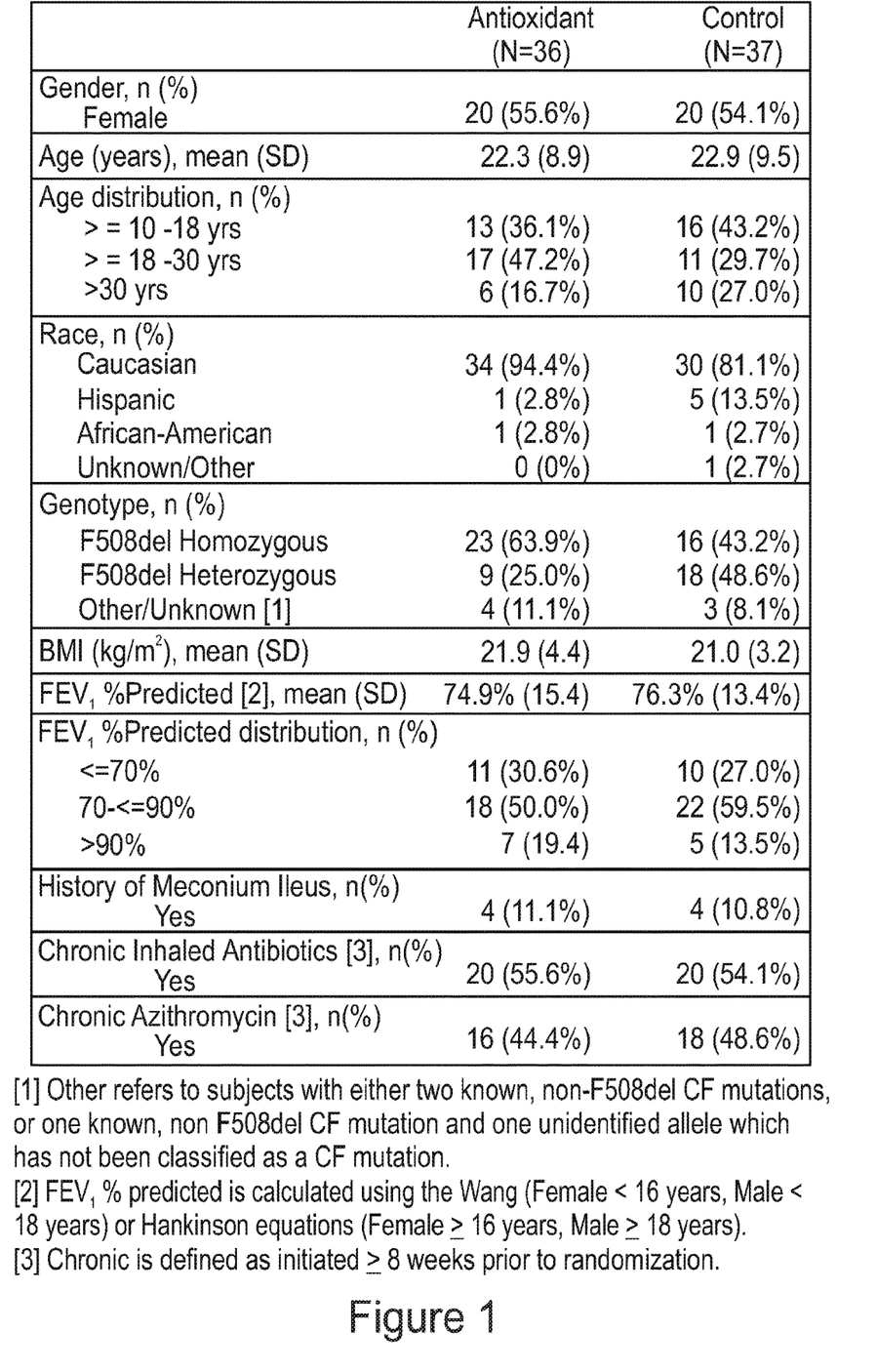
FIG. 1 is a table summarizing clinical characteristics of study participants at randomization.
Figure 2:
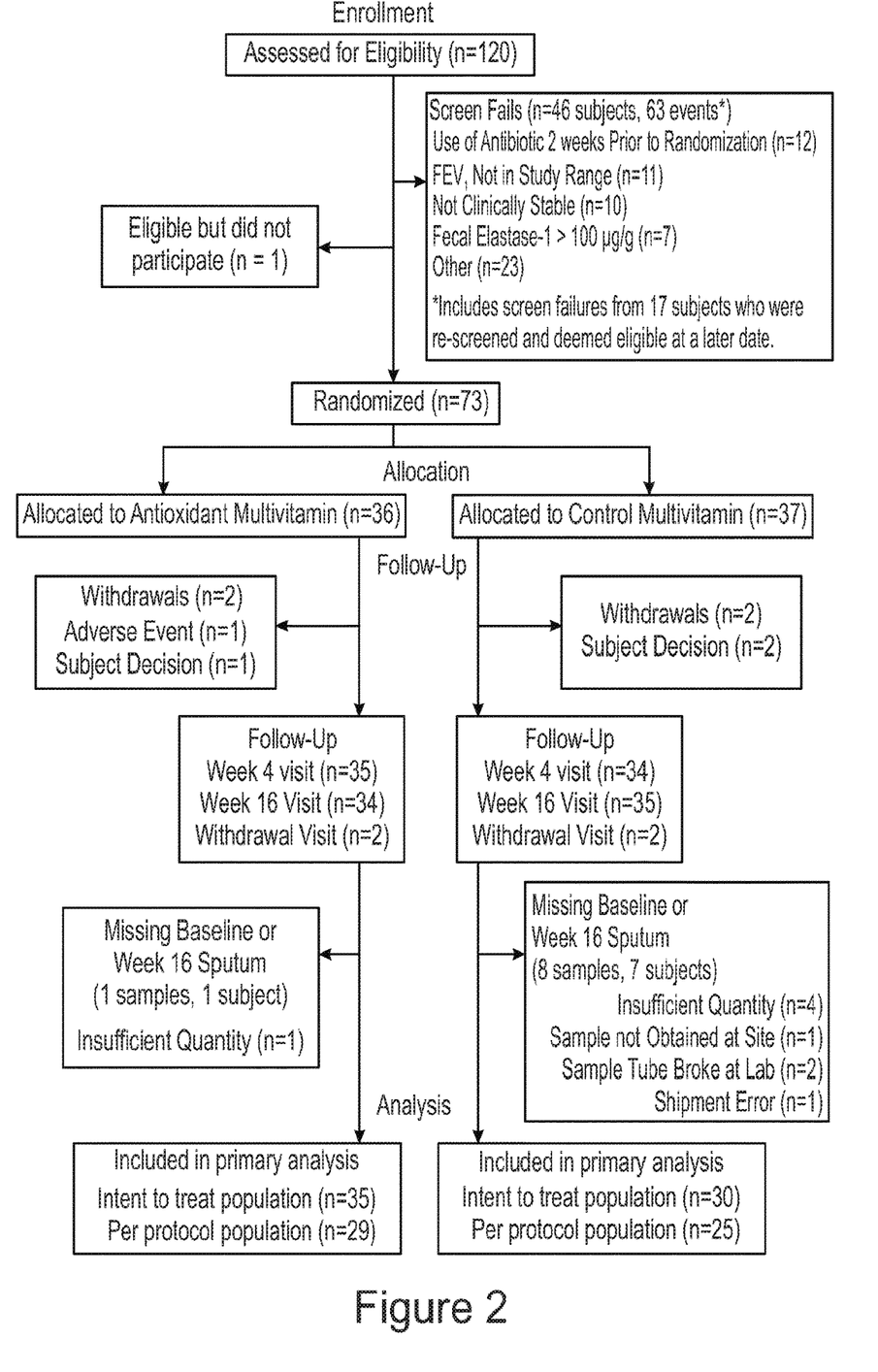
FIG. 2 is a flow-chart representing an overview of the clinical trial procedure.

Subjects who were 10 years of age and older with an FEV1 between 40-100% predicted were eligible to participate. FIG. 1 summarizes clinical characteristics of study participants and randomization. There were four study visits in the trial. Participants were instructed to discontinue their current vitamin supplementation and take a control multivitamin at the screening visit. At Visit 2, subjects were randomized 1:1 to receive either the antioxidant-enriched multivitamin (2 softgels daily) or continue on the control multivitamin (2 softgels daily). The study was stratified on the following factors: age (10-17 years, ≥18 years), FEV1% predicted (40-70%, >70-100%), chronic use of inhaled antibiotics (yes, no), and chronic use of azithromycin (yes, no). Antioxidant and vitamin levels and markers of inflammation and oxidative stress, anthropometric measures, and pulmonary function were obtained at baseline, 4 and 16 weeks. Induced sputum and urine specimens, for markers of inflammation and oxidative stress, were collected at baseline and week 16. FIG. 2 provides an overview of the clinical trial process.

Figure 3:
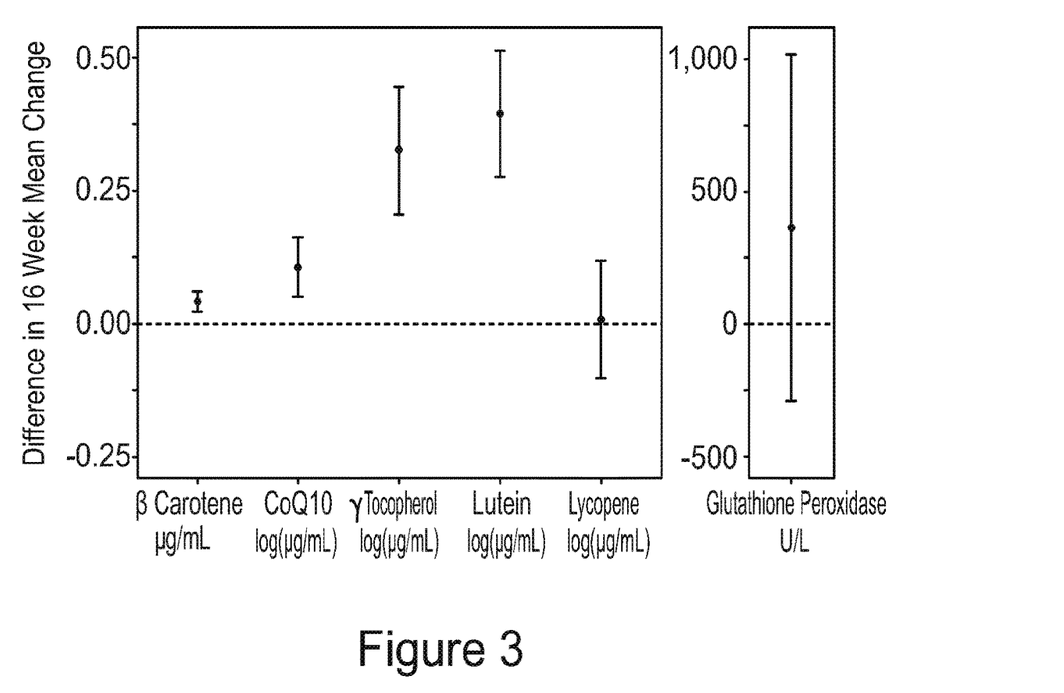
FIG. 3 depicts the changes in concentration of various antioxidants in subject samples after 16 weeks treatment with study formulation.

As shown in FIG. 3, antioxidant levels of beta-carotene, coenzyme Q10, gamma-tocopherol and lutein significantly increased in the antioxidant treated group (p<0.001). No significant changes in measures of inflammation and oxidative stress. The antioxidant-treated group had a lower risk of time to first pulmonary exacerbation requiring antibiotics (hazard ratio=0.50, p=0.04) and a trend toward fewer exacerbations compared with controls.

Figure 4:
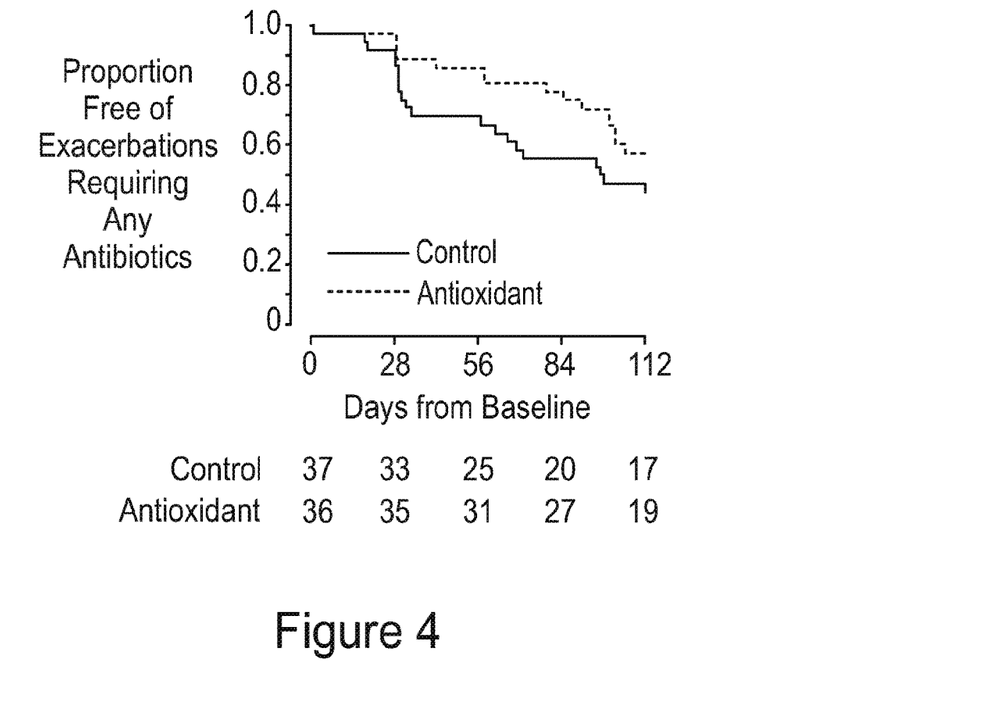
FIG. 4 depicts a comparison of the risk of time to first pulmonary exacerbation between control and test populations, wherein the test population received the study formulation comprising antioxidants.

The statistically significant lower risk of time to first pulmonary exacerbation requiring antibiotics is an important and meaningful clinical outcome. (See FIG. 4). The large reduction in risk of time to first exacerbation with this formulation compares to approved pharmaceutical preparations commonly used in this population including recombinant human deoxyribonuclease (rhDNase), azithromycin, and lumacaftor-ivacaftor. Furthermore, this positive effect of this formulation was observed in cystic fibrosis subjects who were intensely treated with many other anti-inflammatory medications including, steroids, ibuprofen, and inhaled anti-pseudomonal antibiotics and chronic azithromycin therapy (nearly half the subjects).

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A method of reducing the risk of pulmonary exacerbation in a subject suffering from cystic fibrosis, the method comprising administering to the subject an oral dosage form of a multivitamin consisting of:
    about 18,167 IU of a combination of vitamin A and a precursor of vitamin A, comprising about 8% retinyl palmitate and about 92% beta-carotene;
    about 75 mg vitamin C;
    about 3,000 IU vitamin D;
    about 150 IU vitamin E, wherein the vitamin E comprises a combination of about 80 mg mixed tocopherols and about 200 mg d-α-tocopherol polyethylene glycol 1000 succinate (TPGS);
    about 1 mg vitamin K;
    about 1.5 mg thiamin;
    about 1.7 mg riboflavin;
    about 10 mg niacin;
    about 1.9 mg vitamin B6;
    about 200 mcg folic acid;
    about 12 mcg vitamin B12;
    about 100 mcg biotin;
    about 12 mg pantothenic acid;
    about 10 mg zinc;
    about 75 mcg selenium;
    about 10 mg coenzyme Q10;
    about 5 mg lutein;
    about 1 mg lycopene; and
    about 0.75 mg zeaxanthin,
wherein the multivitamin is administered twice daily for a period of at least 8 weeks.

2. The method according to claim 1, wherein the oral dosage form is selected from the group consisting of a tablet and a softgel.

* * * * *